(12) United States Patent
Pfleger et al.

(10) Patent No.: US 9,668,648 B2
(45) Date of Patent: Jun. 6, 2017

(54) SPECTACLES AND METHOD FOR DETERMINING THE PUPIL CENTER OF BOTH OF THE WEARER'S EYES

(71) Applicants: Ernst Pfleger, Vienna (AT); Christoph Pfleger, Vienna (AT)

(72) Inventors: Ernst Pfleger, Vienna (AT); Christoph Pfleger, Vienna (AT)

(*) Notice: Subject to any disclaimer, the term of this patent is extended or adjusted under 35 U.S.C. 154(b) by 0 days.

(21) Appl. No.: 14/913,633

(22) PCT Filed: May 5, 2014

(86) PCT No.: PCT/AT2014/000107
§ 371 (c)(1),
(2) Date: Feb. 22, 2016

(87) PCT Pub. No.: WO2015/024031
PCT Pub. Date: Feb. 26, 2015

(65) Prior Publication Data
US 2016/0206196 A1 Jul. 21, 2016

(30) Foreign Application Priority Data

Aug. 23, 2013 (AT) .................................. A 657/2013

(51) Int. Cl.
| | |
|---|---|
| *A61B 3/14* | (2006.01) |
| *G02C 5/18* | (2006.01) |
| *A61B 3/11* | (2006.01) |
| *A61B 3/113* | (2006.01) |
| *G02C 11/00* | (2006.01) |

(Continued)

(52) U.S. Cl.
CPC ............ *A61B 3/111* (2013.01); *A61B 3/0025* (2013.01); *A61B 3/0091* (2013.01); *A61B 3/113* (2013.01); *A61B 3/145* (2013.01); *G02B 27/0093* (2013.01); *G02C 5/02* (2013.01); *G02C 5/12* (2013.01); *G02C 5/126* (2013.01);

(Continued)

(58) Field of Classification Search
USPC .......................... 351/200–246, 107, 128–134
See application file for complete search history.

(56) References Cited

U.S. PATENT DOCUMENTS

| | | | |
|---|---|---|---|
| 4,300,818 A | 11/1981 | Schachar | |
| 4,762,407 A * | 8/1988 | Anger .................. | G02C 13/003 351/200 |

(Continued)

FOREIGN PATENT DOCUMENTS

| | | |
|---|---|---|
| CN | 202057914 | 11/2011 |
| EP | 2 499 960 | 9/2012 |

(Continued)

OTHER PUBLICATIONS

International Search Report issued by the European Patent Office in International Application PCT/AT2014/000107 on Jan. 13, 2015.

*Primary Examiner* — Mohammed Hasan
(74) *Attorney, Agent, or Firm* — Henry M. Feiereisen LLC (57) ABSTRACT

The invention relates to a pair of spectacles (1) comprising a frame (2), said frame (2) having at least one lens-receiving opening (3) for a lens, and having a right nose section (5) of the frame and a left nose section (6) of the frame, wherein a right eye-capturing camera (7) is arranged in the right nose section (5) of the frame, and a left eye-capturing camera (8) is arranged in the left nose section (6) of the frame.

19 Claims, 5 Drawing Sheets

(51) Int. Cl.
*G02B 27/00* (2006.01)
*A61B 3/00* (2006.01)
*G02C 5/02* (2006.01)
*G02C 5/12* (2006.01)
*G02C 7/08* (2006.01)
*G02C 13/00* (2006.01)

(52) U.S. Cl.
CPC .............. *G02C 7/081* (2013.01); *G02C 11/10* (2013.01); *G02C 13/005* (2013.01)

(56) References Cited

U.S. PATENT DOCUMENTS

| | | |
|---|---|---|
| 6,997,556 B2 | 2/2006 | Pfleger |
| 8,379,918 B2 | 2/2013 | Pfleger et al. |
| 2010/0183205 A1 | 7/2010 | Pfleger et al. |
| 2012/0294478 A1 | 11/2012 | Publicover et al. |
| 2015/0244910 A1* | 8/2015 | Marston ................. G02C 11/10 348/294 |

FOREIGN PATENT DOCUMENTS

| | | |
|---|---|---|
| EP | 2 499 964 | 9/2012 |
| JP | 2005-312605 | 11/2005 |
| WO | WO 2013/067230 | 5/2013 |

* cited by examiner

SPECTACLES AND METHOD FOR DETERMINING THE PUPIL CENTER OF BOTH OF THE WEARER'S EYES

CROSS-REFERENCES TO RELATED APPLICATIONS

This application is the U.S. National Stage of International Application No. PCT/AT2014/000107, filed May 5, 2014, which designated the United States and has been published as International Publication No. WO 2015/024031 and which claims the priority of Austrian Patent Application, Serial No. A 657/2013, filed Aug. 23, 2013, pursuant to 35 U.S.C. 119(a)-(d).

BACKGROUND OF THE INVENTION

The invention relates to spectacles.

Spectacles are known which have a camera, which is oriented onto an eye of the relevant spectacles wearer. By recording an eye video, the coordinates of the pupil and the viewing direction of the eye can be ascertained using such spectacles. Together with a so-called field of vision video, which is prepared by a further field of vision camera arranged on the spectacles in the viewing direction of a user, the point at which the user looks can be ascertained using such spectacles.

Such known spectacles have the disadvantage that the arrangement of the camera can itself result in impairment of the behavior of the user. Such spectacles are generally conceived as a measurement device or research utensil and are also clearly recognizable as such. Test persons do accept the relevant spectacles in regions separated from public view, such as a vehicle or a special test environment, but, above all in environments in which the relevant test person has to act unshielded from other surrounding people, they result in an influence of the behavior of the test person and the persons in the surroundings. The feedback which a human receives from the reactions of his surroundings to his own appearance often has a direct influence on the behavior of the relevant person. This influence leads via the unconscious and therefore withdraws direct control by the relevant person. Publicly wearing a clearly recognizable and striking apparatus on the head results in reactions of the surroundings, which in turn can have direct influence on the behavior, also the viewing behavior, of the relevant test person. In difficult test situations in this regard, this can result in a high level of influence of the test result by way of the means of the test itself.

Such known spectacles record the eye of the test person from the bottom front. It has been shown that this camera position can have negative effects on the accuracy and quality of the achieved measurement results.

These known spectacles additionally have the disadvantage that the protruding parts, such as cameras and cables, restrict the possible uses of such known spectacles to the research uses. For example, such spectacles represent a substantial risk of accident in the surroundings of rapidly rotating machines. Pieces of clothing or equipment objects worn on the body having loops or protruding parts are forbidden in numerous work environments for reasons of safety.

SUMMARY OF THE INVENTION

The object of the present invention is therefore to specify spectacles of the type mentioned at the outset, using which the mentioned disadvantages can be avoided, and which have a high level of measurement accuracy in the detection of the pupils of a test subject, using which the influence of the spectacles themselves on the viewing behavior of the test subject can be reduced, and which are usable in hazardous surroundings.

According to one aspect of the invention, the object is achieved by a pair of spectacles having a frame, wherein the frame has at least one lens receptacle opening for a disk-like structure, wherein the frame has a right nose frame part and a left nose frame part, wherein a right eye acquisition camera is arranged in the right nose frame part, and a left eye acquisition camera is arranged in the left nose frame part.

A detection of the viewing direction of both eyes of a test subject can thus be performed, wherein the test subject remain substantially uninfluenced by the measurement structure. Better detection of the viewing direction of a test subject can thus be performed than in the case of recording only one eye. Due to the so-called binocular measurement, on the one hand, the measurement in the middle region, therefore, in a region of the eye position in which both eyes are visible by way of the eye acquisition camera assigned to the respective eye, can be performed with previously unachieved accuracy, and at the same time in the case of so-called lateral position of the eye, therefore, in situations in which the test subject more or less looks "out of the corner of his eye", a measurement can be performed at all for the first time. Due to the detection of both eyes from the region of the nose rest or nose frame part, at any time at least one of the eyes can be recorded from an angle advantageous for the measurement accuracy, whereby good measurement results can be achieved.

By arranging the eye acquisition camera in the nose frame part, influence of the pupil detection by eyelashes surrounding the eye can be reduced. Furthermore, the influence of interfering reflections on the pupils can thus be reduced. The blinking of the test subject can also be recognized more exactly than previously by detecting both eyes of a test subject.

The focal distance can also be determined by the detection of both pupils of a test subject, therefore, the distance at which the relevant test subject focuses. In this case, by comparing the measurement to the measured values ascertained for the individual eyes, eye misalignments can also be recognized rapidly and easily. For this purpose, it can be necessary to calibrate the relevant spectacles in each case individually to the eyes of the test subject. Furthermore, measurements can be carried out on individual eyes using the present spectacles, for example, in that the other eye is covered in each case.

By illuminating the eyes using an infrared radiation source in a darkened environment, an analysis of the retina or other parts of the eye can additionally be performed using the present spectacles.

By arranging the eye acquisition camera in the nose frame part, spectacles can be provided which have a high level of measurement accuracy with respect to the viewing direction of the eyes of a user, and which can be worn inconspicuously, so that no influence of the behavior of the user is provided because of wearing the spectacles. Thus, above all in the case of public use of the spectacles, significantly improved results can be achieved, since both the measurement accuracy is increased, and the measurement apparatus can now no longer be perceived by the surroundings and therefore also does not result in negative influences of the test person. Due to the integration of the eye acquisition camera into the nose frame part, the spectacles do not have any protruding parts, and are therefore suitable to be worn as work spectacles or protective spectacles. The viewing movements of a worker or a person operating a machine can thus not only be monitored and analyzed, but rather also can be used directly for controlling the machine. In addition, the capability for controlling a machine can thus be monitored, because the physical and mental state of the relevant human can be concluded on the basis of the eye movements, for example, whether he is overtired or is under the influence of psychotropic substances.

The invention furthermore relates to a method for determining pupil center points of both eyes of a human.

The object of the invention is therefore to specify a method of the above-mentioned type, using which the disadvantages mentioned at the outset can be avoided, and using which the viewing direction, the focal distance, and the blinking of a human can be detected.

According to another aspect of the invention, the object is achieved by a method for determining pupil center points of both eyes of a human, wherein the human wears spectacles as set forth above, wherein the right pupil of the human is acquired by the right eye acquisition camera, wherein the right eye acquisition camera prepares a right eye video having successive right individual images, wherein right pupil coordinates of a focal point—corresponding to the right pupil center point—are ascertained from the right individual images, wherein the left pupil of the human is acquired by the left eye acquisition camera, wherein the left eye acquisition camera prepares a left eye video consisting of successive left eye images, wherein pupil coordinates of a focal point—corresponding to the left pupil center point—of the left pupil are ascertained from the left eye images, and wherein the right pupil center point and/or the left pupil center point is/are stored and/or output.

A detection of the viewing direction of both eyes of a human can thus be acquired. The viewing direction of a human can thus be determined with a high level of accuracy. Additionally or alternatively, the focus distance or the focal distance of the eyes of the relevant human can thus be ascertained. A blink can thus be recognized as a spontaneous blink, whereby different states of the relevant human can be reliably differentiated, for example, between a state of high concentration and a state of fatigue.

The dependent claims relate to further advantageous embodiments of the invention.

Reference is hereby expressly made to the wording of the patent claims, whereby the claims are incorporated into the description by reference at this point and are considered to be reproduced verbatim.

BRIEF DESCRIPTION OF THE DRAWING

The invention will be described in greater detail with reference to the appended drawings, in which an embodiment, which is solely a preferred embodiment, is shown as an example. In the Figs..

DETAILED DESCRIPTION OF PREFERRED EMBODIMENTS

FIGS. 1 to 10 show spectacles 1 having a frame 2, wherein the frame 2 has at least one lens receptacle opening 3 for a disk-like structure, and wherein the frame 2 has a right nose frame part 5 and a left nose frame part 6, wherein a right eye acquisition camera 7 is arranged in the right nose frame part 5, and a left eye acquisition camera 8 is arranged in the left nose frame part 6.

A detection of the viewing direction of both eyes 24 of a test subject can thus be performed, wherein he remains substantially uninfluenced by the measurement structure. A better detection of the viewing direction of a test subject can thus be performed than in the case of recording only one eye 24. Due to the so-called binocular measurement, on the one hand, the measurement in the middle region, therefore in a region of the eye position in which both eyes 24 are visible by way of the eye acquisition camera 7, 8 assigned to the respective eye 24, can be performed with previously underachieved accuracy, and at the same time, with so-called lateral position of the eyes 24, therefore in situations in which the test subject more or less looks "out of the corner of his eye", a measurement can be performed at all for the first time. By way of the detection of both eyes 24 from the region of the nose rest or nose frame parts 5, 6, at any time, at least one of the eyes 24 can be recorded from an angle advantageous for the measurement accuracy, whereby good measurement results can be achieved.

Due to the arrangement of the eye acquisition cameras 7, 8 in the nose frame parts 5, 6, influence of the pupil detection by eyelashes surrounding the eye 24 can be reduced. Furthermore, the influence of interfering reflections on the pupils can thus be reduced. The blinking of the test subject can also be recognized more exactly than previously by the detection of both eyes 24 of a test subject.

The focus distance, therefore the distance at which the relevant test subject focuses, can also be determined by the detection of both pupils of a test subject. In this case, eye misalignments can also be recognized rapidly and easily by comparing the measurement to the measured values ascertained for the individual eyes 24. For this purpose, it can be necessary to calibrate the relevant spectacles individually in each case to the eyes 24 of the test subject. Furthermore, measurements on individual eyes 24 can be carried out using the present spectacles 1, for example, in that the other eye 24 is covered in each case.

By illuminating the eyes 24 using an infrared radiation source in a darkened environment, an analysis of the retina can additionally be performed using the present spectacles.

By arranging the eye acquisition cameras 7, 8 in the nose frame parts 5, 6, spectacles 1 can be provided, which have a high measurement accuracy with regard to the viewing direction of the eyes 24 of a user, and which can be worn inconspicuously, so that no influence of the behavior of the user is provided because of wearing the spectacles 1. Thus, above all in the case of public use of the spectacles 1, significantly improved results can be achieved, because the measurement accuracy is increased, and also the measurement apparatus can now no longer be perceived by the surroundings and therefore also does not result in negative influences of the test person. Due to the integration of the eye acquisition cameras 7, 8 in the nose frame parts 5, 6, the spectacles 1 do not have any protruding parts, and are therefore suitable to be worn as work spectacles or protective spectacles. The viewing movements of a worker or of a human operating a machine can thus not only be monitored and analyzed, but rather can be used directly for controlling the machine. In addition, the capability for controlling a machine can thus be monitored, since the physical and mental state of the relevant human can be concluded on the basis of the eye movements, for example, whether he is overtired or under the influence of psychotropic substances.

The specifications "right" or "left" relate to the intended manner of wearing the spectacles 1 by a human.

The present invention relates to spectacles 1 to be worn on the head of a human. The spectacles 1 have a frame 2, which can also be referred to as the middle part. Furthermore, the spectacles 1 have a first earpiece 15 and a second earpiece 16, which are connected to the frame 2. The two earpieces 15, 16 are preferably integrally molded on the middle part, for example, while forming a flexible region, which enables bending of the earpieces 15, 16. It can also be provided that the two earpieces 15, 16 are connected to the middle part by means of a hinge. The earpieces 15, 16 are provided for the purpose, as known per se, of holding the spectacles 1 on the head of the wearer, for example, in that they are formed to engage behind the ears of the human wearing the spectacles 1.

The frame 2 and the two earpieces 15, 16 are preferably formed comprising a plastic.

The frame 2 has at least one lens receptacle opening 3, in which a disk-like structure is preferably arranged, this disk-like structure also being referred to colloquially and independently of the material thereof as a glass or spectacle lens. According to the illustrated preferred embodiment, it is provided that the spectacles 1 have two lens receptacle openings 3, and one disk-like structure is arranged in each of the two lens receptacle openings 3. The disk-like structures can also be optical and/or tinted disk-like structures. Such viewing analyses are also possible in the case of wearers of optical spectacles by the present spectacles 1.

The frame 2 has, in a way known per se, a U-shaped nose receptacle recess, which is provided for arranging the spectacles 1 on the nose of a human. The regions of the frame 2 which laterally border this recess are referred to as the right nose frame part 5 and the left nose frame part 6. The right and the left nose frame parts 5, 6 are preferably regions of the frame 2 enclosing the lens receptacle openings 3 which merge directly and/or integrally into the further regions of the frame 2. The nose frame parts 5, 6 can also be referred to as nose part frames 5, 6.

It can also be provided that the frame 2 does not enclose the at least one lens receptacle opening 3 on all sides, and the lens receptacle opening 3 is therefore designed as a rimless recess.

The surface which is provided for direct contact with the nose of the spectacles-wearing human is referred to as the nose rest surface 20. It can be provided that these nose rest surfaces 20 are formed as integral parts of the frame 2. It is preferably provided that the spectacles 1 have at least one nose bridge receptacle 11, for accommodating at least one nose bridge 12.

The nose bridge receptacle 11 is arranged in this case in or on the U-shaped nose receptacle recess of the frame 2. In this case, the nose bridge receptacle 11 has a part of a catch connection, and the nose bridges 12 provided to be arranged in the nose bridge receptacle 11 have the corresponding other part of such a catch connection.

It is preferably provided that the spectacles, as shown in the Figs., only have a single nose bridge receptacle 11, in which a one-piece U-shaped nose bridge 12 is arranged, which is also referred to as a saddle bridge. However, it can also be provided that a nose bridge receptacle 11 is arranged in each case on each of the two nose frame parts 5, 6, for accommodating one nose bridge 12 each. Different-shaped nose bridges 12 can be used in the spectacles 1 by way of the nose bridge receptacle 11, and the spectacles can thus be adapted to different nose geometries, whereby the spectacles 1 can be adapted using simple means to different humans, wherein it can also be provided in particular that nose bridges 12 are intentionally adapted to single individuals. The spectacles 1 can be provided in a set or system together with different-shaped nose bridges 12, for pre-definable adaptation of the spectacles 1 to different persons by replacement of the nose bridges 12. The at least one nose bridge 12 is preferably formed comprising silicone and/or an elastomer.

It is provided that a right eye acquisition camera 7 is arranged in the right nose frame part 5, and a left eye acquisition camera 8 is arranged in the left nose frame part 6. The two eye acquisition cameras 7, 8 are arranged in this case in the parts of the frame 2 which are arranged closest to the nose receptacle recess. The two eye acquisition cameras 7, 8 are designed as digital cameras and have an objective lens. The two eye acquisition cameras 7, 8 are each provided to film one eye of the human wearing the relevant spectacles 1, and to prepare in each case an eye video including individual eye images or individual images.

A primary purpose of the eye acquisition cameras 7, 8 is to acquire the pupil of the human wearing the spectacles 1. It is therefore sufficient if the entire eye cannot be acquired by the respective eye acquisition camera 7, 8, but rather only a region around the pupil of the respective eye. The eye acquisition cameras 7, 8 can also be referred to as pupil acquisition cameras. The eye acquisition cameras 7, 8 have a suitable focal length to acquire the corresponding regions of the eye from the position in the nose frame part. The focal length and the aperture angle which can be acquired using a focal length are dependent on the sensor size of the camera and can be selected without problems by the embodying person skilled in the art using the present specifications.

The right eye acquisition camera 7 is oriented onto a right region 9, in which, when the spectacles 1 are arranged on the head of a human, the right eye 24 of this human is at least regionally arranged in a variety of humans. Correspondingly, the left eye acquisition camera 8 is oriented onto a left region, in which, in a variety of humans, the left eye of the human is at least regionally arranged. The position of the right region 9 and the left region, and therefore the viewing direction of the two eye acquisition cameras 7, 8, are individually different. However, there are statistic probabilities depending on sex and ethnic affiliation with respect to the position of the eyes and also the nose geometry, which enable the viewing direction of the two eye acquisition cameras 7, 8 to be specified, at least for individual regions or countries, such that the relevant spectacles are matching for a large number of humans in the relevant region.

Figure 8:
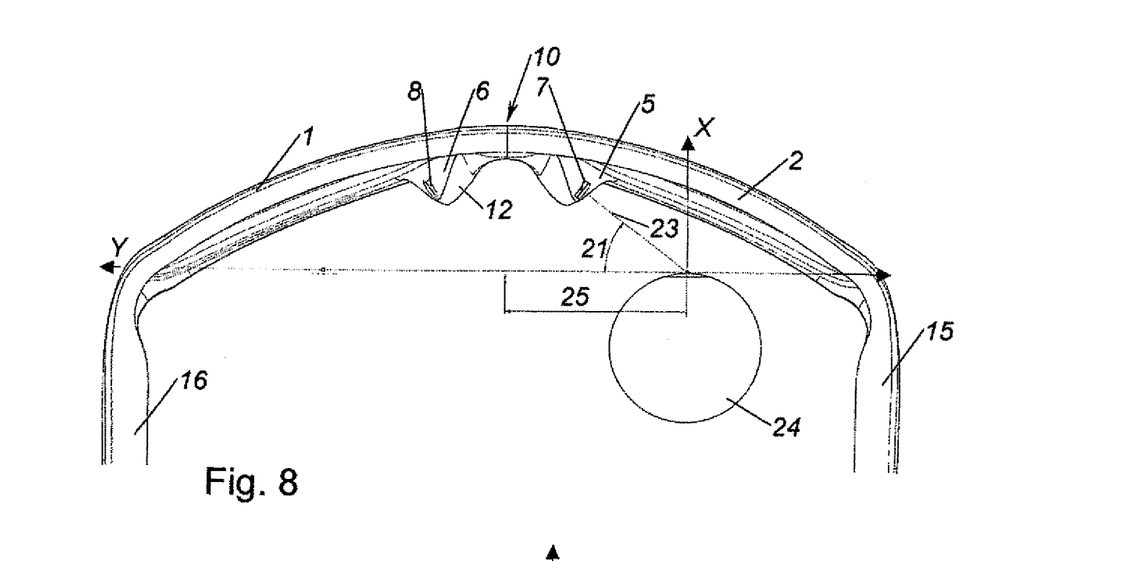
FIG. 8 shows a detail of spectacles according to FIG. 1 in horizontal projection.

According to one preferred embodiment of the present spectacles, it is provided that the right region 9 is arranged between 20 mm and 40 mm, in particular between 25 mm and 35 mm, to the right of a spectacles center 10, the corresponding distance 25 is shown in FIG. 8, and is arranged spaced apart between 10 mm and 25 mm from the right eye acquisition camera 7, and the left region is arranged between 20 mm and 40 mm, in particular between 25 mm and 35 mm, to the left of the spectacles center 10, and spaced apart between 10 mm and 25 mm from the left eye acquisition camera 8. Because spectacles 1 are generally constructed symmetrically, they also have an unambiguously defined center. The distance from the eye acquisition cameras 7, 8 is to be measured in the direction of the extension of the earpieces 15, 16 or the head receptacle region of the spectacles 1. A good basic adaptation to the head shape in Europe and North America can be achieved by the specified values. Spectacles for the Asiatic, African, Latin American, or Pacific region are accordingly to be designed using other values, in consideration of the specifications of the subject matter.

Figure 9:
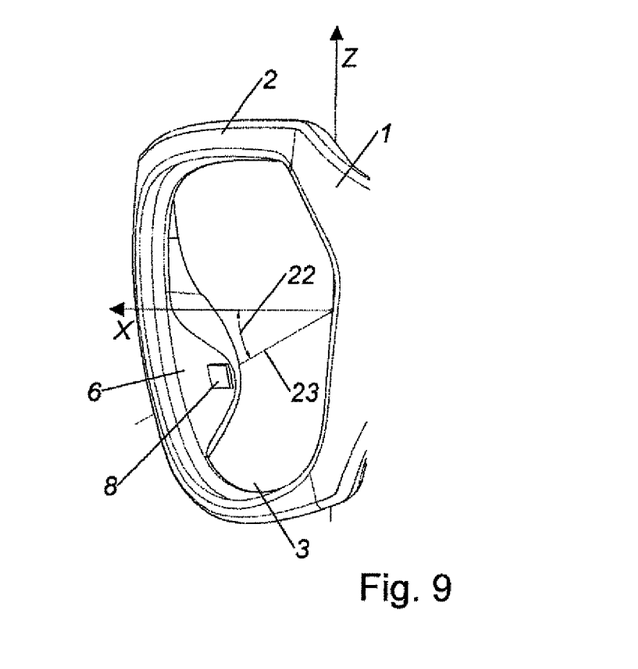
FIG. 9 shows a detail of spectacles according to FIG. 1 in a side view.
Figure 10:
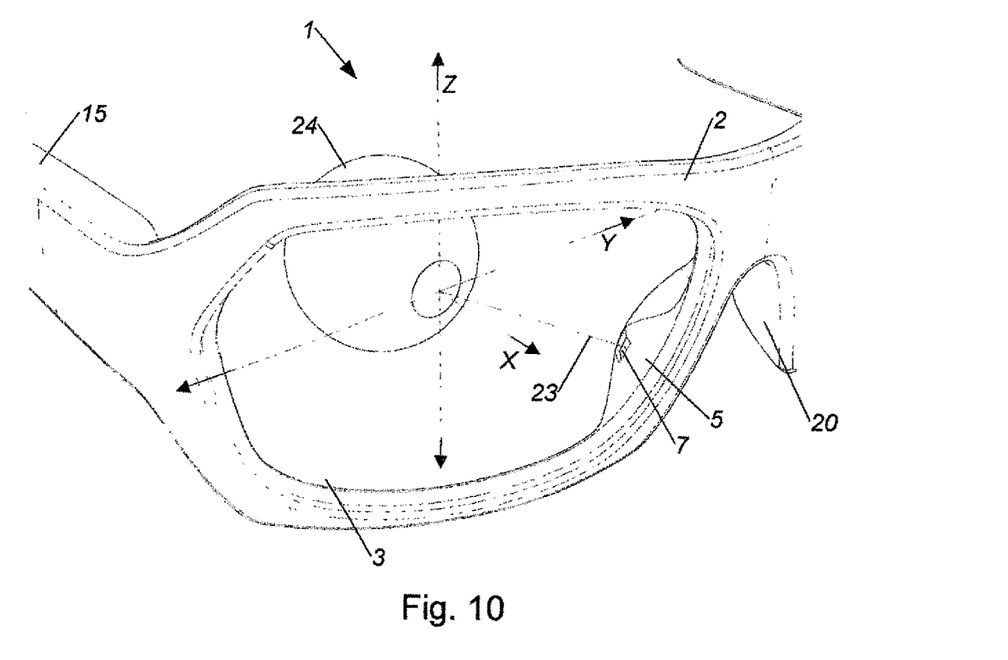
FIG. 10 shows a detail of spectacles according to FIG. 1 in a fourth axonometric illustration.

FIGS. 8, 9, and 10 each show detail views of the present spectacles 1. A coordinate system is shown in the relevant FIGS. 8, 9, and 10. Proceeding from the symmetry of the relevant spectacles 1, this coordinate system was selected such that the YZ plane spanned by the Y axis and the Z axis on the right and left sides of the spectacles each intersect opposing or symmetrically-arranged regions. The XZ plane spanned by the X axis and the Z axis is arranged on the YZ plane perpendicularly and in parallel to the plane of symmetry of the spectacles. The XY plane is arranged perpendicularly to the YZ plane and the XZ plane. The right eye acquisition camera 7 and the left eye acquisition camera 8 are each arranged inclined in relation to these planes or axes. In this case, according to one preferred embodiment, it is provided that in each case one optical axis 23 of the two eye acquisition cameras 7, 8 is arranged at a first angle 21 in relation to the Y axis, and the first angle 21 is between 30° and 50°. Furthermore, it is provided according to the preferred embodiment that in each case one optical axis 23 of the two eye acquisition cameras 7, 8 is arranged at a second angle 22 in relation to the X axis, and the second angle 22 is between 25° and 35°.

Different nose bridges 12 can be used for adapting the spectacles 1, as already described. Alternatively and/or additionally thereto, it can be provided that the right eye acquisition camera 7 and/or the left eye acquisition camera 8 are arranged so they are pivotable about at least one axis, in particular about two axes, in the right nose frame part 5 or the left nose frame part 6. The viewing direction of the right and/or left eye acquisition camera 7, 8 can thus be adjusted. An adaptation of the spectacles 1 to different head shapes is thus possible.

According to one preferred embodiment of present spectacles 1, it is provided that at least one field of vision camera 13 is arranged on the frame 2. The field of vision camera 13 is provided to record a field of vision video including individual and successive field of vision images. The recordings of the two eye acquisition cameras 7, 8 and the at least one field of vision camera 13 can thus be entered in correlation in the field of vision video of the respective viewpoint. The field of vision camera 13 is only explicitly shown in FIG. 1 on the spectacles 1.

It is preferably provided that the at least one field of vision camera 13 is arranged in a region or a bridge between the right nose frame part 5 and the left nose frame part 6. A larger number of field of vision cameras 13 can also be arranged in the spectacles 1, wherein in particular one left and one right field of vision camera is provided in the frame 2 in each case in the region of the transition to the first or second earpiece 15, 16, respectively.

It is preferably provided that the spectacles 1 have a data processing unit 17 and a data interface 18, the data processing unit 17 is connected to the right eye acquisition camera 7 and the left eye acquisition camera 8, the spectacles 1 furthermore have an energy accumulator 19 for the energy supply of the right eye acquisition camera 7 and the left eye acquisition camera 8, and also the data processing unit 17 and the data interface 18.

According to one particularly preferred embodiment of present spectacles 1 it is provided that the data processing unit 17 and the data interface 18 are arranged in the first earpiece 15, and the energy accumulator 19 is arranged in the second earpiece 16. In this case, the first earpiece 15 can either be the right or the left earpiece, and vice versa. The entire recording, initial analysis, and storage of the recorded videos can thus be performed in or by the spectacles 1 themselves. Interfering connections can thus be omitted.

Figure 1:
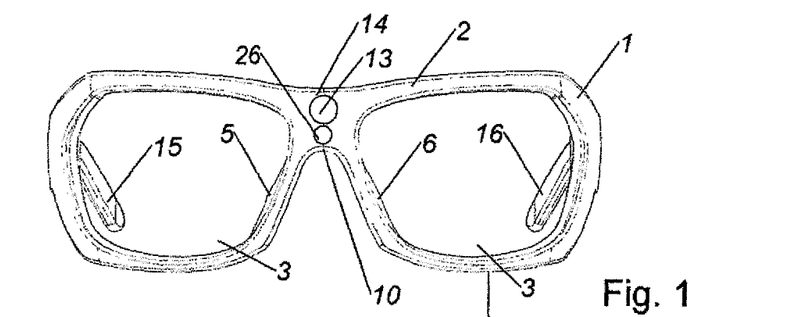
FIG. 1 shows a preferred embodiment of present spectacles in outline.
Figure 2:
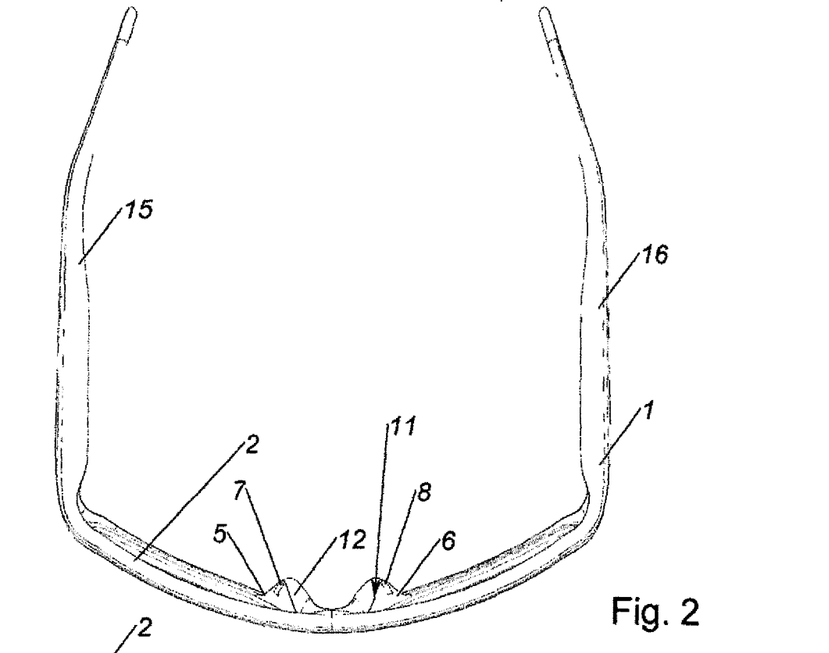
FIG. 2 shows the spectacles according to FIG. 1 in horizontal projection.
Figure 3:
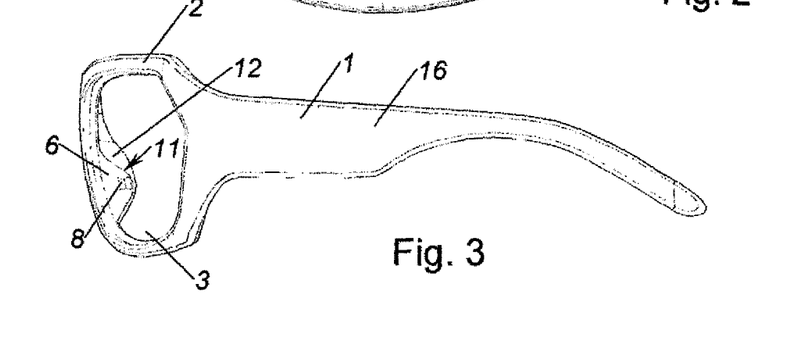
FIG. 3 shows the spectacles according to FIG. 1 in a side view.
Figure 4:
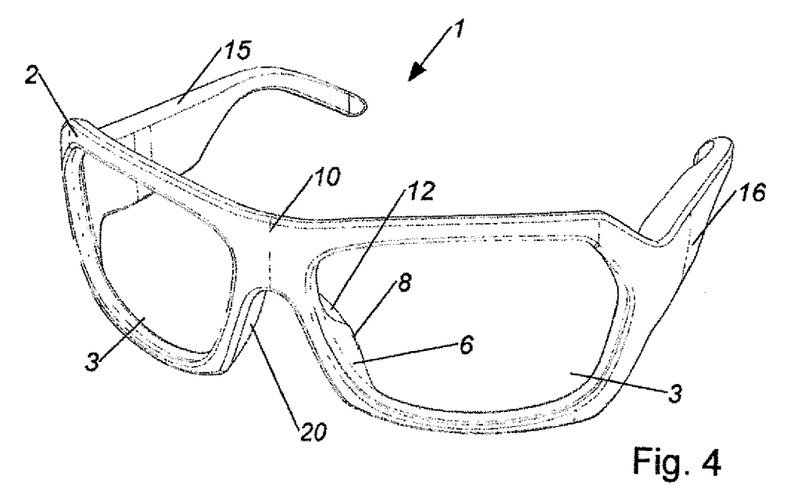
FIG. 4 shows the spectacles according to FIG. 1 in a first axonometric illustration.
Figure 5:
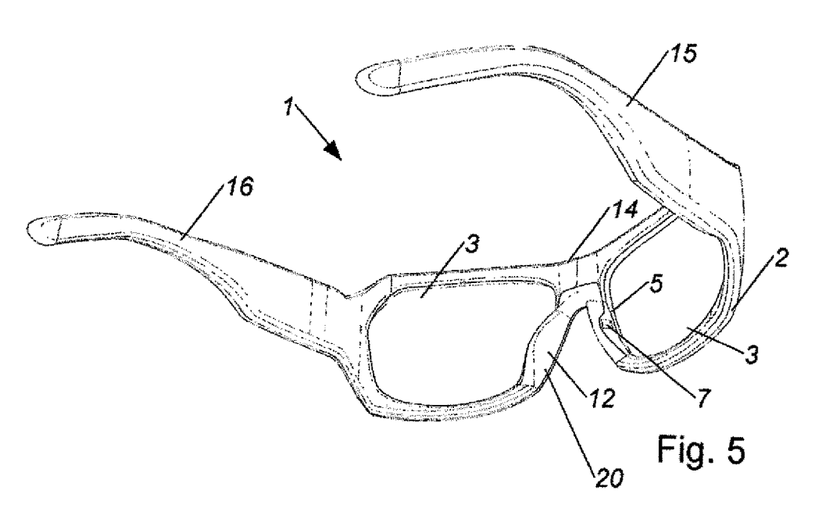
FIG. 5 shows the spectacles according to FIG. 1 in a second axonometric illustration.
Figure 6:
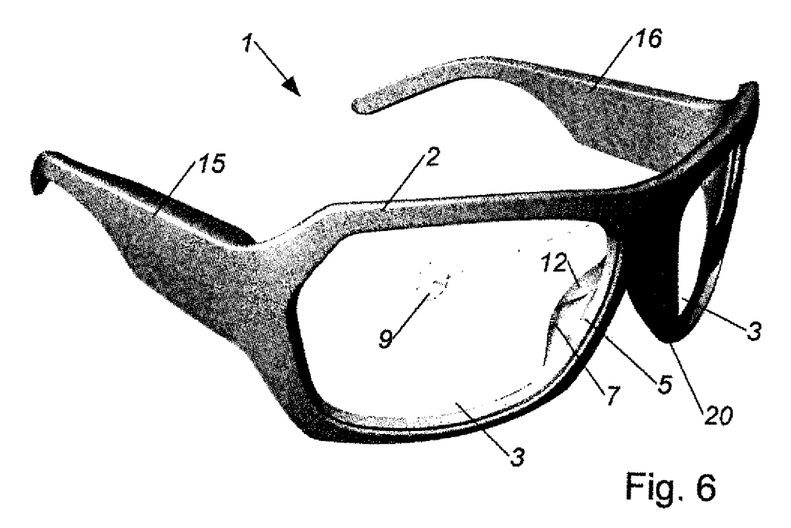
FIG. 6 shows the spectacles according to FIG. 1 in a third axonometric illustration.
Figure 7:
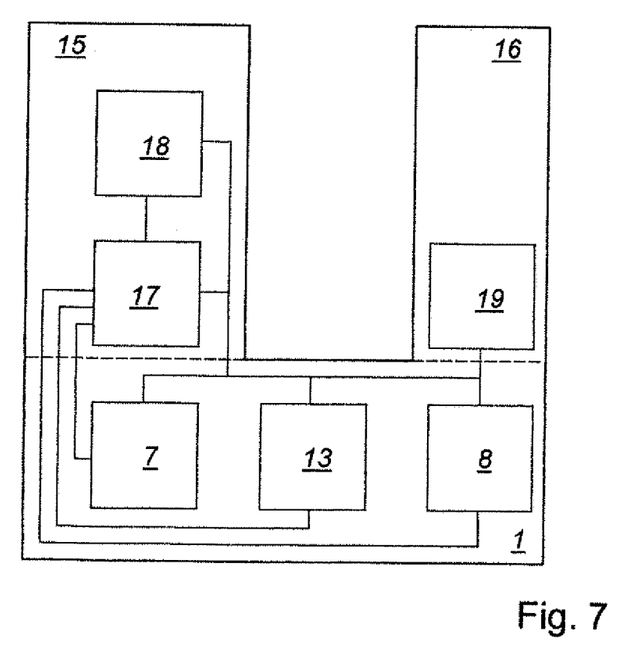
FIG. 7 shows a block diagram of a preferred embodiment of present spectacles.

FIG. 7 shows a block diagram of correspondingly designed spectacles 1, wherein the external contours of the block diagram are to symbolize the spectacles 1. The three cameras, the field of vision camera 13, the right eye acquisition camera 7, and the left eye acquisition camera 8, are arranged in the middle part or frame 2. They are preferably at least indirectly connected by circuitry to the energy accumulator 19, which is preferably designed as a battery, arranged in the second earpiece 16. A data processing unit 17, which also comprises a data memory, is arranged in the first earpiece 15. It is preferably designed as a combination of a microcontroller or DSP together with a RAM. The data processing unit 17 is connected in a signal-conducting manner to a data interface 18. It can also be provided that the data interface 18 and the data processing unit 17 are formed jointly in hardware, for example, by an ASIC or an FPGA. The interface is preferably designed as a wireless interface, for example, according to the Bluetooth standard or IEEE 802.x, or as a wired interface, for example, according to the USB standard, wherein in this case the spectacles 1 have a corresponding socket, for example, according to micro-USB. The data processing unit 17 and the data interface 18 are connected at least indirectly to the energy accumulator 19 by circuitry, and are connected in a signal-conducting manner to the three cameras, the field of vision camera 13, the right eye acquisition camera 7, and the left eye acquisition camera 8.

As already described, the present described spectacles 1 are particularly well suitable for carrying out a method for determining pupil center points of both eyes of a human. In this case, it is provided that the right pupil of the human is acquired by the right eye acquisition camera 7, wherein the right eye acquisition camera 7 prepares a right eye video including successive right individual images, wherein the right pupil coordinates within the right eye images of a focal point—corresponding to the right pupil center point—of the right pupil are ascertained from the right eye images, wherein the left pupil of the human is acquired by the left eye acquisition camera 8, wherein the left eye acquisition camera 8 prepares a left eye video including successive left individual images, wherein pupil coordinates within the left eye images of a focal point—corresponding to the left pupil center point—of the left pupil are ascertained from the left eye images, and wherein the right pupil center point and/or the left pupil center point is/are stored and/or output.

A detection of the viewing direction of both eyes 24 can thus be acquired. The viewing direction of a human can thus be determined with a high level of accuracy. Additionally or alternatively, the focus distance or the focal distance of the eyes of the relevant human can thus be ascertained. A blink can thus be recognized as a spontaneous blink, whereby it is possible to differentiate reliably between different states of the relevant human, for example, between a state of high concentration and a state of fatigue.

It is preferably provided that a computer objective lens distortion correction is carried out in each case for the two eye acquisition cameras 7, 8 and the field of vision camera 13, as well as a correction of prospective distortions.

The two eye videos and the field of vision video are recorded in chronological synchronization, which is controlled by the data processing unit 17.

The ascertainment of the pupil coordinates and the correlation with a field of vision video, as is also preferably provided in the present spectacles 1 or present method, is described in EP 1 300 018 B1.

In the preferred method, the precise pupil coordinates of the pupil center point in the eye video are ascertained by an image recognition program. In this case, the pupil coordinates are ascertained for each individual image of the eye video. The ascertainment of the pupil coordinates is preferably performed automatically using an image recognition program. For this purpose, for each individual image of the eye video, the contrasts of the pupils to the surroundings are registered and all points of the individual image which are darker than a set degree of darkness are searched for. Using these points, a dark area is completely acquired and delimited, and the focal point of this dark area is then automatically ascertained. Because the dark area corresponds to the pupil of the test person, the focal point of the dark area represents the pupa center point. The image recognition program preferably offers setting variants for the corresponding contrast and the degree of darkness, so that a particularly high level of accuracy can be achieved for all individual images. As already noted above, points can additionally be selected on the edge of the pupil, which can be identified particularly well and reliably because of the contrast to the surroundings, and these points can be taken as part of an ellipse, whereupon the focal point or center point of an ellipse is calculated, on the circumference of which the pre-definable number of points also lie. For each individual image, the best contrast in each case in the form of a grayscale value threshold can therefore be ensured for different lighting conditions, which makes reliable determination of the pupil coordinates possible overall. The grayscale value threshold is the value which is, for example, in digitized form between 1 and 256 and defines the percentage proportion of black or white on a pixel. The highest achievable value corresponds to solid black, and the lowest value to white. Because the pupil presumably never reaches the solid black value during the recording, a value is to be defined which—at least for this image—corresponds to the real existing pupil gray. The threshold value excludes all pixels which are brighter than the defined gray value, all darker regions are used for finding the focal point. Three parameters enable the threshold definition to be optimized. Because the lighting conditions often change very strongly during the experiments within the sequence, this threshold value definition is preferably also possible individually for each image. All settings can be stored in accordance with the high requirements for each image of the sequence in a file.

Proceeding from the ascertained pupil coordinates, the file can be processed further differently, for example, by the correlation described in EP 1 300 018 B1 with a field of vision video, which is prepared by the field of vision camera.

It is preferably provided that the spectacles 1 are calibrated on the basis of a pre-definable viewing sequence before ascertaining the pupil center points. For this purpose, firstly one or more pattern viewing sequences of the test person on one or more specific predefined control points are recorded. A pattern viewing sequence is to be understood as a viewing sequence which is recorded solely for the calibration, and during which the test person looks at predefined control points. For example, a specific control point can be marked on a wall. To obtain the best possible contrast, for example, a black marking on an otherwise white surface can be selected as a control point. The control point is generally a cross or a spot of light or the like. The test person is instructed to fix on this control point, wherein the field of vision and the eye of the test person are recorded by the two eye acquisition cameras and the field of vision camera. The control points to be targeted are additionally preferably arranged at different defined intervals.

According to a preferred refinement of the present spectacles, it is provided that at least one illuminant 26, in particular an LED, is arranged on a front side of the spectacles 1, and the illuminant 26 is connected to the data processing unit 17 and the energy accumulator 19. In this case, the side facing away from the wearer of the spectacles 1 is identified as the front side of the spectacles 1. Simple and automatable calibration of the spectacles 1 is possible by way of the illuminant 26. The illuminant is controlled for this purpose by the data processing unit 17.

It is preferably provided in this case that a reflective surface, in particular a mirror, is arranged opposite to the human wearing the spectacles, or the relevant human is placed in front of a mirror, and the illuminant 26 is activated for the calibration of the spectacles 1. The relevant human now observes his image in the mirror and fixes on the image of the illuminant in this case. By pre-definable variation of the position of the head with continuous fixation on the illuminant image in the mirror, the positions of the pupils change in relation to the spectacles 1 or the eye acquisition cameras 7, 8. Because the wavelength or color of the illuminant 26 is known, it can be easily recognized by the field of vision camera 13 and the data processing unit 17.

As already mentioned, it is possible, using the present spectacles 1 and the above-described method in the refinement thereof, to recognize a spontaneous blink as such, in contrast, for example, to the lid movements as are triggered by a foreign body entering the eye. It is provided in this case that furthermore, the right eyelids are detected in the successive right individual images, wherein the left eyelids are detected in the successive left individual images, and wherein, when a right eyelid conceals the right pupil center point in a right individual image and a left eyelid conceals the left pupil center point in one of the individual images, a message of a spontaneous blink is generated and output and/or stored. The relevant right and left individual images which are set forth in the mentioned condition are each individual images recorded substantially simultaneously with respect to time.

To detect the eyelids, it is provided that firstly the respective pupils are completely acquired. By means of an image processing program having pattern recognition, it is easily possible to recognize the concealment of the pupil continuously progressing from one image to the next as such and to differentiate it from a highlight. A regional concealment of the respective pupils can be easily and reliably assigned to a blink in this manner.

In a refinement of the relevant method for the method for recognizing a spontaneous blink, it is furthermore provided that a visual downtime between the beginning of a spontaneous blink and the end of the same spontaneous blink is measured, and if a limiting time is exceeded by the visual downtime, a warning message is generated and/or output. The physical and/or mental state of a human can thus be easily monitored. Present spectacles 1 can thus monitor, in cooperation with a machine, whether the human operating the machine applies the attentiveness considered to be required for this activity. Thus, for example, the spectacles 1 can analyze on the basis of the blinking activities of the relevant operator whether he is overtired, and safe further operation of the machine is endangered. The spectacles 1 can then, for example, emit a warning message to turn off the relevant machine or can trigger other switching procedures.

In a refinement of the method for determining the pupil center points of both eyes of a human, it is provided that furthermore the focus distance of a human is ascertained, wherein an interocular distance is ascertained from the pupil coordinates in the individual images of the field of vision video, wherein a right viewing angle is assigned to the right pupil coordinates, wherein a left viewing angle is assigned to the left pupil coordinates, and wherein the focus distance is ascertained from the interocular distance, the right viewing angle, and the left viewing angle, and is preferably stored and/or output. In particular, switching pulses or switching commands can be generated and output in this case.

In this case, to ascertain the focus distance, the interocular distance and the respective viewing angle of the two eyes are ascertained. The interocular distance forms the base of an imaginary triangle, wherein the viewing angles of the two eyes represent the angles which the two sides occupy in relation to the base. The height of the relevant triangle can be easily ascertained therefrom as the focus distance or focal distance, where it can be established more accurately at which point a human is actually looking.

In addition, misalignments of the eyes can be recognized easily and reliably by individual measurements on the two eyes of a test subject. It can be necessary in this case to calibrate the eye acquisition cameras 7, 8 separately in each case for the two eyes, for example, in that one eye is covered.

According to one advantageous refinement of the invention, it can be provided that the ascertained focus distance is used to set or control lenses, which are arranged in the lens receptacle openings 3, having variable or pre-definably variable geometry. It is preferably provided in this case that the at least one lens is connected to the data processing unit 17. To set the relevant geometric parameters on the relevant lens, it is necessary for the respective focus distances or distance intervals to be determined to be stored in the memory assigned to the data processing unit 17. The relevant parameters can each contain multiple variables for each focus distance in this case. To set the geometry of the relevant lenses, it is preferably provided that at least one value, which is associated with the ascertained focus distance, for the geometric determination of the lens having pre-definable variable geometry is taken from the data memory, and the geometry of the lens is set on the basis of the value. Spectacles 1 can thus be provided, which can provide reliable aid even in the case of complicated visual impairments.

In addition, anomalies, predominantly in the pupils and/or iris region, can be recognized from the images of the two eyes.

In conjunction with pre-definable experimental sequences to be carried out, the navigation structures or patterns of the eyes can be recorded simultaneously. In addition, they can be analyzed and compared, so that real ophthalmological initial examinations are possible.

What is claimed is:

1. A pair of spectacles, comprising:
   a frame including at least one opening for receiving a disk-like structure, said frame including a right nose frame part and a left nose frame part;
   a right eye acquisition camera arranged in the right nose frame part and configured to prepare a right eye video comprised of successive right individual images, wherein the right eye acquisition camera is oriented on a right region arranged between 20 mm and 40 mm, in particular between 25 mm and 35 mm, to the right of a center of the spectacles and spaced at a distance between 10 mm and 20 mm from the right eye acquisition camera, said left eye acquisition camera being oriented on a left region arranged between 20 mm and 40 mm, in particular between 25 mm and 35 mm, to the left of the center of the spectacles and spaced at a distance between 10 mm and 20 mm from the left eye acquisition camera; and
   a left eye acquisition camera arranged in the left nose frame part and configured to prepare a left eye video comprised of successive left individual images.

2. The spectacles of claim 1, wherein at least one of the right eye acquisition camera and the left eye acquisition camera is arranged so as to be pivotable about at least one axis, in particular about two axes, in the right nose frame part or the left nose frame part, respectively.

3. The spectacles of claim 1, further comprising at least one nose bridge receptacle configured to accommodate at least one nose bridge, designed in particular as a saddle bridge.

4. The spectacles of claim 1, further comprising at least one field of vision camera arranged on the frame.

5. The spectacles of claim 4, wherein the at least one field of vision camera is arranged in a region between the right nose frame part and the left nose frame part.

6. The spectacles of claim 1, wherein the frame has a U-shaped nose receptacle recess for arranging the spectacles on the nose of a human, the right nose frame part and the left nose frame part laterally bordering the nose receptacle recess.

7. A pair of spectacles, comprising:
   a frame including at least one opening for receiving a disk-like structure, said frame including a right nose frame part and a left nose frame part;
   a right eye acquisition camera arranged in the right nose frame part and configured to prepare a right eye video comprised of successive right individual images; and
   a left eye acquisition camera arranged in the left nose frame part and configured to prepare a left eye video comprised of successive left individual images;
   a data processing unit connected to the right eye acquisition camera and the left eye acquisition camera;
   a data interface;
   an energy accumulator configured to supply energy to the right eye acquisition camera, the left eye acquisition camera, the data processing unit, and the data interface,
   wherein preferably the data processing unit and the data interface are arranged in a first earpiece, which is connected to the frame, and
   wherein preferably the energy accumulator is arranged in a second earpiece, which is connected to the frame.

8. The spectacles of claim 7, further comprising at least one illuminant, in particular an LED, arranged on a front side of the spectacles, said illuminant being connected to the data processing unit and the energy accumulator.

9. The spectacles of claim 7, wherein the disk-like structure is a lens having a pre-definable changeable geometry and is connected to the data processing unit.

10. A system, comprising:
a pair of spectacles, said spectacles comprising a frame including at least one opening for receiving a disk-like structure, said frame including a right nose frame part and a left nose frame part, a right eye acquisition camera arranged in the right nose frame part and configured to prepare a right eye video comprised of successive right individual images, a left eye acquisition camera arranged in the left nose frame part and configured to prepare a left eye video comprised of successive left individual images, and at least one nose bridge receptacle; and
a pre-definable number of different shaped nose bridges, each configured for accommodation in the at least one nose bridge receptacle to enable pre-definable adaptation of the spectacles to different persons by replacement of the nose bridges.

11. A method for determining pupil center points of both eyes of a human wearing a pair of spectacles, comprising:
acquiring the right pupil of the human by a right eye acquisition camera of the spectacles to thereby prepare a right eye video comprised of successive right individual images;
ascertaining right pupil coordinates of a focal point in correspondence to a right pupil center point from the right individual images;
acquiring the left pupil of the human by a left eye acquisition camera of the spectacles to thereby prepare a left eye video comprised of successive left eye images;
ascertaining pupil coordinates of a focal point in correspondence to a left pupil center point of the left pupil from the left eye images;
storing or outputting the right pupil center point and/or the left pupil center point;
arranging a reflective surface opposite to the human wearing the spectacles to calibrate the spectacles;
activating an illuminant arranged on a front side of the spectacles; and
having the human observe an image of the illuminant on the reflective surface, thereby moving the head of the human into pre-definable positions while fixing the image of the illuminant.

12. The method of claim 11, wherein ascertaining the pupil coordinates for each individual image of the eye video, includes an image recognition program to automatically
register contrasts of the pupil to the surroundings,
search of the individual image all points which are darker than a set degree of darkness,
acquire and delimit a dark area corresponding to the pupil using these points, and
ascertain the focal point of the dark area, which corresponds to the pupil center point having the pupil coordinates.

13. A method for determining a spontaneous blink of a human wearing a pair of spectacles, comprising:
acquiring the right pupil of the human by a right eye acquisition camera of the spectacles to thereby prepare a right eye video comprised of successive right individual images;
ascertaining right pupil coordinates of a focal point in correspondence to a right pupil center point from the right individual images;
acquiring the left pupil of the human by a left eye acquisition camera of the spectacles to thereby prepare a left eye video comprised of successive left eye images;
ascertaining pupil coordinates of a focal point in correspondence to a left pupil center point of the left pupil from the left eye images;
storing or outputting the right pupil center point and/or the left pupil center point;
detecting the right eyelids of the human in the successive right eye images;
detecting the left eyelids of the human in the successive left eye images; and
generating and outputting and/or storing a report of a spontaneous blink, when a right eyelid conceals the right pupil center point in a right eye image and a left eyelid conceals the left pupil center point in a left eye image.

14. The method of claim 13, further comprising measuring a visual downtime between the beginning of a spontaneous blink and the end of the same spontaneous blink, and generating and/or outputting a warning message when a visual downtime exceeds a limiting time.

15. The method of claim 13, wherein ascertaining the pupil coordinates for each individual image of the eye video, includes an image recognition program to automatically
register contrasts of the pupil to the surroundings,
search of the individual image all points which are darker than a set degree of darkness,
acquire and delimit a dark area corresponding to the pupil using these points, and
ascertain the focal point of the dark area, which corresponds to the pupil center point having the pupil coordinates.

16. A method for ascertaining a focus distance of a human wearing a pair of spectacles, comprising: acquiring the right pupil of the human by a right eye acquisition camera of the spectacles to thereby prepare a right eye video comprised of successive right individual images; ascertaining right pupil coordinates of a focal point in correspondence to a right pupil center point from the right individual images; acquiring the left pupil of the human by a left eye acquisition camera of the spectacles to thereby prepare a left eye video comprised of successive left eye images; ascertaining pupil coordinates of a focal point in correspondence to a left pupil center point of the left pupil from the left eye images; storing or outputting the right pupil center point and/or the left pupil center point; ascertaining an intraocular distance from the pupil coordinates; assigning a right viewing angle to the right pupil coordinates; assigning a left viewing angle to the left pupil coordinates; and ascertaining the focus distance from an interocular distance, the right viewing angle, and the left viewing angle.

17. The method of claim 16, further comprising storing the focus distance in particular as a switching pulse.

18. The method of claim 16, further comprising taking at least one value, which is associated with the focus distance, from a data memory of a data processing unit for geometrical determination of a lens, which is arranged in a lens receptacle opening of the spectacles and has a pre-definable variable geometry, and setting the geometry of the lens as a function of the value.

19. The method of claim 16, wherein ascertaining the pupil coordinates for each individual image of the eye video, includes an image recognition program to automatically

- register contrasts of the pupil to the surroundings,
- search of the individual image all points which are darker than a set degree of darkness,
- acquire and delimit a dark area corresponding to the pupil using these points, and
- ascertain the focal point of the dark area, which corresponds to the pupil center point having the pupil coordinates.

* * * * *